United States Patent [19]
Tomer et al.

[11] Patent Number: 6,162,438
[45] Date of Patent: Dec. 19, 2000

[54] HERBAL COMPOSITIONS AND THEIR USE AS AGENTS FOR CONTROL OF HYPERTENSION, HYPERCHOLESTEROLEMIA AND HYPERLIPIDEMIA

[75] Inventors: Onkar S. Tomer, Watchung; Peter Glomski, South Amboy; Kripanath Borah, Morris Plains, all of N.J.

[73] Assignee: Chromak Research, Inc., Bound Brook, N.J.

[21] Appl. No.: 09/344,165

[22] Filed: Jun. 24, 1999

[51] Int. Cl.$^7$ ..................................................... A61K 35/78
[52] U.S. Cl. ............................................................ 424/195.1
[58] Field of Search ........................................... 424/195.1

[56] References Cited

U.S. PATENT DOCUMENTS

| | | |
|---|---|---|
| 4,917,921 | 4/1990 | Hermes . |
| 5,108,750 | 4/1992 | Liu . |
| 5,120,538 | 6/1992 | Oei . |
| 5,494,668 | 2/1996 | Patwardhan . |
| 5,529,778 | 6/1996 | Rohatgi . |
| 5,658,571 | 8/1997 | Gopalan et al. . |
| 5,683,698 | 11/1997 | Chavali et al. . |
| 5,707,631 | 1/1998 | Lieberman . |
| 5,900,240 | 5/1999 | Tomer et al. . |
| 5,958,417 | 9/1999 | Hsu . |

OTHER PUBLICATIONS

Kraft, Phytomedicine, vol. 4, No. 4, pp. 369–378, 1997.
Shaila et al., International Journal of Pharmacognosy, vol. 35, No. 4, pp. 126–129, 1997.
Tanabe et al., Chemical and Pharmaceutical Bullentin (Tokyo), vol. 41, No. 4, pp. 710–713, 1993.
Derwent abstract of Chinese patent, 1,135,338 A, Nov. 1996.
Gulati et al. Indian Journal of Pharmacology, vol. 23, No. 4, pp. 264–267, 1991.

*Primary Examiner*—Francisco Prats
*Assistant Examiner*—Susan D. Coe
*Attorney, Agent, or Firm*—Jack Matalon

[57] ABSTRACT

Edible herbal compositions for use as agents for the control of hypertension, hypercholesterolemia and hyperlipidemia in mammals. The edible composition is a mixture of at least three, preferably at least six, herbs selected from the group consisting of *Terminalia arjuna, Cynara scolymus, Zingibar officinale, Allium sativum, Crataegus oxycantha, Curcuma longa, Boerhaavia diffusa* and *Trigonella foenumgraecum*. The composition preferably contains the herbs in approximately equal amounts.

4 Claims, No Drawings

HERBAL COMPOSITIONS AND THEIR USE AS AGENTS FOR CONTROL OF HYPERTENSION, HYPERCHOLESTEROLEMIA AND HYPERLIPIDEMIA

FIELD OF THE INVENTION

The present invention is directed to edible herbal compositions for use as agents for control of hypertension, hypercholesterolemia and hyperlipidemia in mammals. The composition comprises a synergistic mixture of at least three herbs selected from a group of eight herbs identified below.

BACKGROUND OF THE INVENTION

The prior art is replete with references to herbal medicines for treatment of a variety of ailments in mammals. Typically, such herbal medicines are obtained as the active compound (s) by extraction from plant tissues. Although the use of various herbs have been described in related areas, the synergistic combination of the edible herbs for use as agents for control of hypertension, hypercholesterolemia and hyperlipidemia in mammals has never previously been described.

WO 94/1894 and U.S. Pat. No. 5,707,631 are directed to a therapeutic herbal composition including *Trigonella foenum-graecum* seed, *Syzygium aromataticum* fruit, *Allium sativum* bulb, *Cinnamomum zeylanicum* bark, *Saussurea costus* root and *Euphorbia lathyris* bud; the U.S. patent discloses the foregoing herbs in combination with sodium chloride (preferably sea salt).

There currently exists a great need for non-synthetic, holistic therapeutic compositions for the control of hypertension (i.e. high blood pressure), hypercholesterolemia (high cholesterol levels) and hyperlipidemia (high triglyceride levels) in mammals. It has been found that the herbal compositions of the invention are synergistic in their effect and daily ingestion of such compositions of the invention is an effective therapeutic method of achieving such control without the troublesome side effects on the liver, digestive system and kidneys associated with synthetic drugs.

SUMMARY OF THE INVENTION

This invention describes an edible composition for use as an agent for control of hypertension, hypercholesterolemia and hyperlipidemia in mammals. Since the composition comprises a mixture of herbs as described below, the composition is relatively inexpensive, produces no adverse side effects, may be taken in multiple daily doses over prolonged periods of time and it results in the control of hypertension, hypercholesterolemia and hyperlipidemia within a few weeks after commencement of ingestion of the composition.

DETAILS OF THE INVENTION

The edible composition of the invention comprises a mixture of at least three herbs selected from the group consisting of the following eight herbs:

| Botanical Name | Common Name | Preferred Source |
| --- | --- | --- |
| *Terminalia arjuna* | Arjun bark | bark |
| *Cynaera scolymus* | Artichoke | leaf |
| *Zingibar officinale* | Ginger | rhizome |
| *Allium sativum* | Garlic | bulb |
| *Crataegus oxycaentha* | Hawthorn | leaf, flower, berries |
| *Curcuma longa* | Turmeric | rhizome |
| *Boerhaavia diffusa* | Hogwood | roots |
| *Trigonella foenumgraecum* | Fenugreek | seed |

Preferably, the mixture contains at least six of the above-listed eight herbs. More preferably, the mixture will contain at least the following six herbs: *Terminalia arjuna, Cynera scolymus, Allium salivum, Crataegus oxycentha, Boerhaavia diffusa* and *Trigonella foenumgraecum.*

The ratio of the herbs in the edible composition is not critical, e.g. each herb may be present in amounts as low as 10 wt. %, based on the weight of the composition, with the balance being the other herbs. However, as a matter of convenience, it is preferable that the composition contain approximately equal amounts of each herb.

Preferably, the compositions contain no fillers or enhancing agents, since such materials are unnecessary and merely serve to dilute the effective concentration of the herbs and to decrease the absorption rate into the blood-stream after ingestion.

The individual herbs, obtained from the preferable sources indicated above, may be used in the form of extracts using aqueous and non-aqueous solvents (e.g. ethanol, isopropanol, acetone, etc., which are evaporated off prior to use). Preferably, the herbs are milled and mixed as fine, dry powders. The dry powder mix may then be further processed into the form of compressed tablets, caplets or lozenges or processed into pouches (i.e. "tea" bags) from which water infusions are ingested.

The preferable method of processing the compositions of the invention for ingestion is to package the powdered herbal mixture into gelatin capsules (preferably hard gelatin) of a size preferably of the order of zero or double zero. Such capsules would then contain about 300–600 mg of the powdered herbal mixture per capsule. It has been found that hard gelatin capsules represent the most efficient, economical form of packaging of the edible composition for ingestion.

The dosage of the herbal compositions of the invention to be ingested will vary, depending on factors such as severity of the hypertension, hypercholesterolemia and hyperlipidemia, age, physical condition and body weight of the patient, diet, etc. As a general guide, it is expected that patients with a body weight in the range of 60–90 kg would ingest about 1,000–5,000 mg/day of the herbal compositions (corresponding to 2–12 zero or double zero size hard gelatin capsules per day). Typically, a human patient would ingest about 40 mg of the composition per kg of body weight. It is to he understood that these dosage levels are only general guides and the proper dosage level for individual patients may vary considerably depending on the factors indicated above. However, one benefit of the edible compositions of the present invention is that the dosage is not "critical" as is the case with administration of synthetic pharmaceutical medications such as those mentioned above. Since the edible compositions of the present invention are holistic in nature and represent dietary supplements in their own right, "overdosing" is not a problem. The individual patient with a particular body weight and life style may readily determine the proper dosage by starting out with the general dosage level set forth above and adjust the dosage as necessary to control the hypertension, hypercholesterolemia and hyperlipidemia.

The following non-limiting examples shall serve to illustrate the invention. Unless otherwise indicated, all amounts and parts are on a weight basis.

EXAMPLE 1

Fine powders of *Terminalia arjuna, Cynaera scolymus, Allium sativum, Crataegus oxycantha, Boerhaavia diffusa* and *Trigonella foenumgraecum* were blended in equal amounts of each herb and the blended powder was then used to test the hypercholesterolemia effect in mice. A total of six female mice of strain C57BL/6J-Apoe<tm1Unc was used in this study. This particular strain of mice is traditionally used to test for hypercholesterolemia.

The mice were divided into two groups of three in each group. One group was used as the control and the other group was used to test the effect of the blended herbal powder described above. The control group of mice ingested, by demand feeding, 10–15 ml of plain water per day over a period of time of 8 weeks. The test group of mice ingested the same amount of water per day containing 450 mg/l of the blended herbal powder described above over the same period of time.

Blood samples were taken from the tails of each group of mice periodically over a period of three months. The blood samples were tested for cholesterol level using a diagnostic kit from Chematics Corp. known as "Chemcard Systems". The test is a three-minute test in which whole blood is placed on a test trip and the color is matched against a predetermined color card indicating the cholesterol level in the blood. The results obtained from the control and test groups are set forth below in Table I.

TABLE I

| | Cholesterol Level in Blood, mg/dl | | | |
|---|---|---|---|---|
| Test Period | 1 week | 2 weeks | 3 weeks | 12 weeks |
| Control Group | 300 | 283 | 275 | 292 |
| Test Group | 275 | 242 | 220 | 192 |

The results set forth in Table I indicated that the test group of mice fed with the blended herbal powder exhibited a reduction of cholesterol of more than 30%. Such results prove that the herbal composition of the invention is quite effective in controlling hypercholesterolemia.

EXAMPLE 2

Two human volunteers, one male weighing 160 lb. and one female weighing 140 lb. served as the test subjects for this example; both test subjects had elevated blood cholesterol levels. The test subjects ingested six capsules on a daily basis (three capsules twice per day); each capsule contained 450 mg of the blended herbal powder described in Example 1. The test subjects were monitored over a period of six months; the results of this study are set forth in Table II below.

TABLE II

| | Cholesterol Level in Blood, mg/dl | | |
|---|---|---|---|
| Test Period | Initial | 4 weeks | 26 weeks |
| Male | 240 | | 200 |
| Female | 238 | 225 | 205 |

The results in Table II indicate that for both test subjects, the herbal composition of the invention was effective in reducing the blood cholesterol level by about 15%.

EXAMPLE 3

Two human volunteers, one male weighing 160 lb. and one female weighing 140 lb. served as the test subjects for this example; both test subjects suffered from hypertension. The test subjects ingested a total of six capsules on a daily basis (three capsules twice per day); each capsule contained 450 mg of the blended herbal powder described in Example 1.

The test subjects were monitored over a period of three months; the results of this study are set forth in Table III below.

TABLE III

| | Blood Pressure | | | |
|---|---|---|---|---|
| Subject | Initial | 1 week | 2 weeks | 12 weeks |
| Male | 160/95 | 140/85 | 140/80 | 130/80 |
| Female | 165/95 | 140/90 | 140/80 | 140/80 |

The results set forth in Table III prove that the herbal composition of the invention is quite effective in controlling hypertension.

EXAMPLE 4

In this example, a male human volunteer, weighing approximately 160 lb and suffering from hyperlipidemia, served as the test subject. The test subject ingested six capsules on a daily basis (three capsules twice per day); each capsule contained 450 mg of the blended herbal powder described in Example 1. The test subject was monitored over a period of six months; the results of this study are set forth in Table IV below.

TABLE IV

| | Blood Triglycerides, mg/dl | |
|---|---|---|
| Subject | Initial | 26 weeks |
| Male | 460 | 220 |

The results set forth in Table IV prove that the herbal composition of the invention is quite effective in controlling hyperlipidemia.

What is claimed is:

1. An edible composition for use as an agent for control of hypertension, hypercholesterolemia and hyperlipidemia in mammals comprising a mixture of at least six herbs selected from the group consisting of *Terminalia arjuna, Cynara scolymus, Allium sativum, Crataegus oxycantha, Curcuma longa, Boerhaavia diffusa* and *Trigonella foenumgraecum.*

2. The edible composition of claim 1 wherein the six herbs comprise *Terminalia arjuna, Cynara scolymus, Allium sativum, Crataegus oxycantha, Boerhaavia diffusa* and *Trigonella foenumgraecum.*

3. The composition of claim 1 wherein each of the herbs are present in the mixture in equal amounts.

4. The composition of claim 1 wherein each of the herbs are present in the mixture in an amount of at least 10 wt. %, based on the weight of the composition.

* * * * *